(12) United States Patent
Stoughton et al.

(10) Patent No.: US 8,400,149 B2
(45) Date of Patent: Mar. 19, 2013

(54) SYSTEMS AND METHODS FOR GATING AN IMAGING DEVICE

(75) Inventors: Robert Stoughton, Boulder, CO (US); Paul S. Addison, Edinburgh (GB); James N. Watson, Dunfermline (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 278 days.

(21) Appl. No.: 12/567,287

(22) Filed: Sep. 25, 2009

(65) Prior Publication Data

US 2011/0074409 A1 Mar. 31, 2011

(51) Int. Cl.
*G01V 3/00* (2006.01)

(52) U.S. Cl. .......................... 324/309; 324/318

(58) Field of Classification Search .......... 324/300–322; 600/407–445
See application file for complete search history.

(56) References Cited

U.S. PATENT DOCUMENTS

| | | | |
|---|---|---|---|
| 4,289,141 A | 9/1981 | Cormier | |
| 5,416,582 A | 5/1995 | Knutson et al. | |
| 5,439,483 A | 8/1995 | Duong-Van | |
| 5,590,650 A | 1/1997 | Genova | |
| 5,632,272 A | 5/1997 | Diab et al. | |
| 5,778,881 A | 7/1998 | Sun et al. | |
| 5,795,304 A | 8/1998 | Sun et al. | |
| 5,797,840 A | 8/1998 | Akselrod | |
| 5,827,195 A | 10/1998 | Lander | |
| 5,967,995 A | 10/1999 | Shusterman et al. | |
| 6,002,952 A | 12/1999 | Diab et al. | |
| 6,036,653 A | 3/2000 | Baba et al. | |
| 6,094,592 A | 7/2000 | Yorkey | |
| 6,095,984 A | 8/2000 | Amano et al. | |
| 6,117,075 A | 9/2000 | Barnea | |
| 6,129,675 A | 10/2000 | Jay | |
| 6,135,966 A | 10/2000 | Ko | |
| 6,171,257 B1 | 1/2001 | Weil et al. | |
| 6,171,258 B1 | 1/2001 | Karakasoglu et al. | |
| 6,208,951 B1 | 3/2001 | Kumar et al. | |
| 6,293,915 B1 | 9/2001 | Amano et al. | |
| 6,325,761 B1 | 12/2001 | Jay | |
| 6,337,895 B1 | 1/2002 | Sase | |
| 6,361,501 B1 | 3/2002 | Amano et al. | |
| 6,393,311 B1 | 5/2002 | Edgar, Jr. et al. | |
| 6,535,754 B2 * | 3/2003 | Fishbein et al. | 600/422 |

(Continued)

FOREIGN PATENT DOCUMENTS

JP 09-084776 3/1997
WO WO 01/25802 4/2001

(Continued)

OTHER PUBLICATIONS

Addison, Paul S., The Illustrated Wavelet Transform Handbook, Taylor & Francis Group, 2002.

(Continued)

*Primary Examiner* — Brij Shrivastav

(57) ABSTRACT

A method and system for automatically gating an imaging device is disclosed. Physiological process information of a patient may be derived from a plethysmographic signal, for example, by analyzing the plethysmographic signal transformed by a continuous wavelet transform. Other techniques for deriving physiological process information of a patient include, for example, analyzing a scalogram derived from the continuous wavelet transform. The physiological process information may be used to automatically gate imaging data acquired from an imaging device in order to synchronize the imaging data with the physiological process information.

20 Claims, 13 Drawing Sheets

U.S. PATENT DOCUMENTS

| | | | |
|---|---|---|---|
| 6,561,986 | B2 | 5/2003 | Baura |
| 6,608,934 | B2 | 8/2003 | Scheirer |
| 6,621,889 | B1 | 9/2003 | Mostafavi |
| 6,654,623 | B1 | 11/2003 | Kastle |
| 6,810,277 | B2 | 10/2004 | Edgar, Jr. et al. |
| 6,931,269 | B2 | 8/2005 | Terry |
| 6,937,696 | B1 | 8/2005 | Mostafavi |
| 6,959,266 | B1 | 10/2005 | Mostafavi |
| 7,001,337 | B2 | 2/2006 | Dekker |
| 7,020,507 | B2 | 3/2006 | Scharf |
| 7,035,679 | B2 | 4/2006 | Addison |
| 7,043,293 | B1 | 5/2006 | Baura |
| 7,054,453 | B2 | 5/2006 | Causevic |
| 7,054,454 | B2 | 5/2006 | Causevic et al. |
| 7,079,888 | B2 | 7/2006 | Oung |
| 7,171,269 | B1 | 1/2007 | Addison |
| 7,173,525 | B2 | 2/2007 | Albert |
| 7,191,100 | B2 | 3/2007 | Mostafavi |
| 7,203,267 | B2 | 4/2007 | De Man et al. |
| 7,225,013 | B2 | 5/2007 | Geva et al. |
| 7,254,500 | B2 | 8/2007 | Makeig |
| 7,257,436 | B2 | 8/2007 | Sasaki et al. |
| 7,289,835 | B2 | 10/2007 | Mansfield |
| 7,403,638 | B2 | 7/2008 | Jeung et al. |
| 7,515,949 | B2 | 4/2009 | Norris |
| 7,519,413 | B1 * | 4/2009 | Morris et al. ............. 600/411 |
| 7,519,488 | B2 | 4/2009 | Fu |
| 7,523,011 | B2 | 4/2009 | Akiyama et al. |
| 8,150,128 | B2 * | 4/2012 | Konofagou et al. .......... 382/131 |
| 2003/0163057 | A1 | 8/2003 | Flick et al. |
| 2004/0147832 | A1 * | 7/2004 | Fishbein et al. ............. 600/410 |
| 2005/0043616 | A1 | 2/2005 | Chinchoy |
| 2006/0209631 | A1 | 9/2006 | Melese et al. |
| 2006/0211930 | A1 | 9/2006 | Scharf et al. |
| 2006/0229519 | A1 | 10/2006 | Fujiwara et al. |
| 2006/0258921 | A1 | 11/2006 | Addison et al. |
| 2006/0265022 | A1 | 11/2006 | John et al. |
| 2007/0021673 | A1 | 1/2007 | Arbel et al. |
| 2007/0073120 | A1 | 3/2007 | Li et al. |
| 2007/0073124 | A1 | 3/2007 | Li et al. |
| 2007/0167694 | A1 | 7/2007 | Causevic et al. |
| 2007/0167851 | A1 | 7/2007 | Vitali et al. |
| 2007/0282212 | A1 | 12/2007 | Sierra et al. |
| 2008/0045832 | A1 | 2/2008 | McGrath |
| 2008/0082018 | A1 | 4/2008 | Sackner et al. |
| 2008/0154142 | A1 * | 6/2008 | Lundback ..................... 600/508 |
| 2008/0200797 | A1 * | 8/2008 | Kotmel et al. ................ 600/411 |
| 2008/0214903 | A1 | 9/2008 | Orbach |
| 2008/0243021 | A1 | 10/2008 | Causevic et al. |
| 2008/0319301 | A1 * | 12/2008 | Busse .......................... 600/410 |
| 2009/0088622 | A1 | 4/2009 | Mostafavi |
| 2010/0113902 | A1 * | 5/2010 | Hete et al. .................... 600/323 |

FOREIGN PATENT DOCUMENTS

| | | |
|---|---|---|
| WO | WO 01/62152 | 8/2001 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram In Children," Acta Paediatricia, 2006; 95: 1124-1128.

Yamada, Michio, "Wavelet Analysis and Its Application," Journal of the Institute of Electronics, Information and Communication Engineers, vol. 76, No. 5, May 1993, pp. 518-528.

* cited by examiner

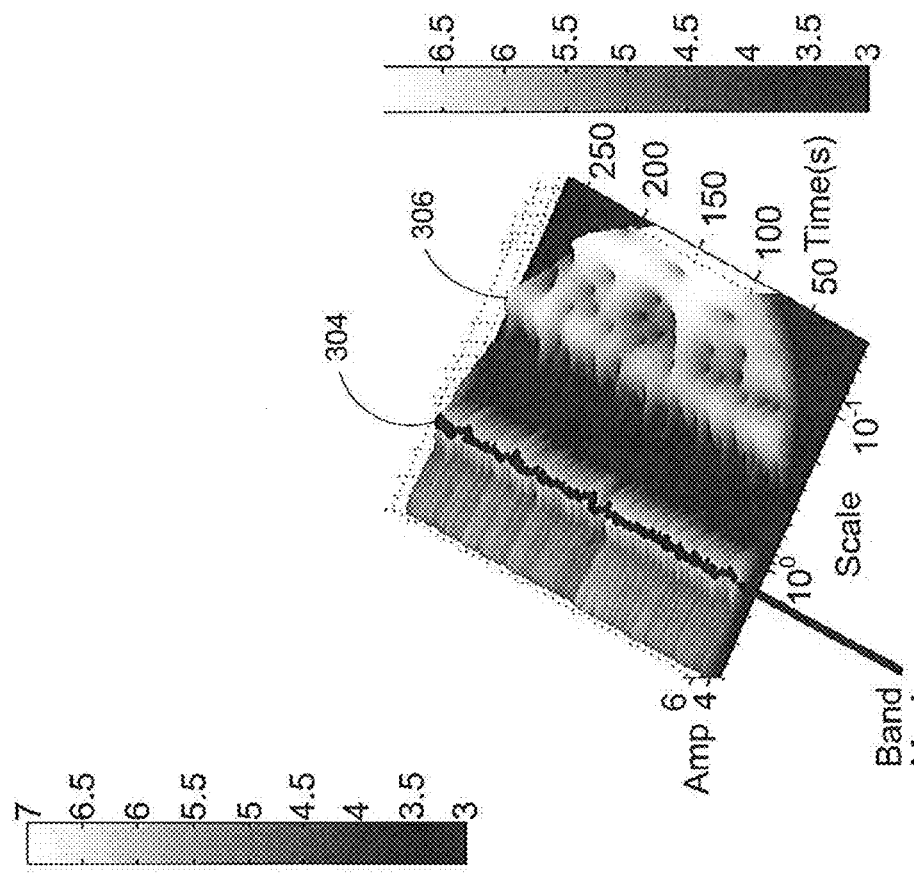
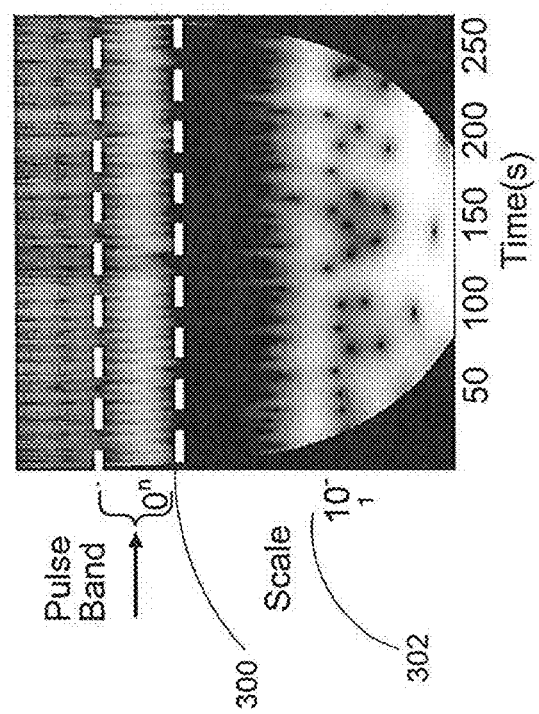
FIG. 3(a)
FIG. 3(b)

SYSTEMS AND METHODS FOR GATING AN IMAGING DEVICE

The present disclosure relates to medical imaging and, more particularly, the present disclosure relates to gating an imaging device based on a plethysmographic signal.

SUMMARY

The analysis of plethysmographic waveform data obtained by pulse oximetry may provide respiration information such as the respiratory rate. Signals that describe where the patient is in the respiratory and/or cardiac cycle may also be derived. These signals may be used to gate the data acquired during a medical imaging scan (e.g., computed tomography (CT), positron emission tomography (PET), magnetic resonance imaging (MRI)) in order to "freeze" the motion of internal organs during the scan.

The present disclosure relates to a device that may use one or more pulse oximeter sensors attached to a patient to derive signals that are proportional to the position within the patient's respiratory and/or cardiac cycle. These signals may be real-time signals representing the current position within the cycle, or the signals may be a datafile representing the time history of the positions within the cycles, or both. These signals may also represent information regarding aperiodic episodes of voluntary or involuntary movement (e.g., coughing) which may allow for further gating during the imaging process and thus a further improvement in image quality. For example, if the time period of motion is known, the length of the scan may be increased as needed to ensure sufficient data is acquired for a high-quality motion-free image. The datafile may include a time marker to allow it to be synchronized with other patient data, such as that obtained from a medical imaging device.

The gating may begin to occur after the system acquires data for some period of time in order to get an estimate of the patient's respiratory cycle. The system may output a "ready" signal when it has acquired sufficient data and is able to output respiratory and/or cardiac cycle position information with a suitable degree of confidence.

In one suitable approach, a continuous wavelet transform of a plethysmographic signal may be performed to better determine characteristic metrics of the plethysmographic signal. For example, a pulse band and a breathing band may be extracted from a scalogram generated from a wavelet-transformed photoplethysmograph signal. The locus of maxima points on the breathing band with respect to scale (the "ridge") may be projected onto a time-scale phase plot. The phase on the ridge may then be extracted, allowing the instantaneous phase of the breathing features to be tracked in time. This allows the phase of the respiration features to be decoupled from the other features in the signal at other scales. In this way, an accurate measure of the instantaneous phase of respiration may be made. This may then be used to gate a patient's respiratory cycle.

Because of the time-scale nature of the transform phase, instantaneous phase values corresponding to the breathing band ridge may be tracked as the respiration rate varies. Any other suitable techniques to track sudden changes in respiration rate may be used, including, for example, the use of average values of phase across time and/or frequency.

Other features in the wavelet transformed signal may also be used to track respiratory cycle including the real and/or imaginary parts of the transform at the scales of interest.

The above described techniques may also be used to gate according to the cardiac cycle. For example, the pulse band ridge may be used to track the instantaneous cardiac phase.

In addition, gating may be based on both the information gained simultaneously on the cardiac cycle and the respiratory cycle.

BRIEF DESCRIPTION OF THE DRAWINGS

The above and other features of the present disclosure, its nature and various advantages will be more apparent upon consideration of the following detailed description, taken in conjunction with the accompanying drawings in which:

FIGS. 3(a) and 3(b) show illustrative views of a scalogram derived from a PPG signal in accordance with an embodiment;

DETAILED DESCRIPTION

Figure 1:
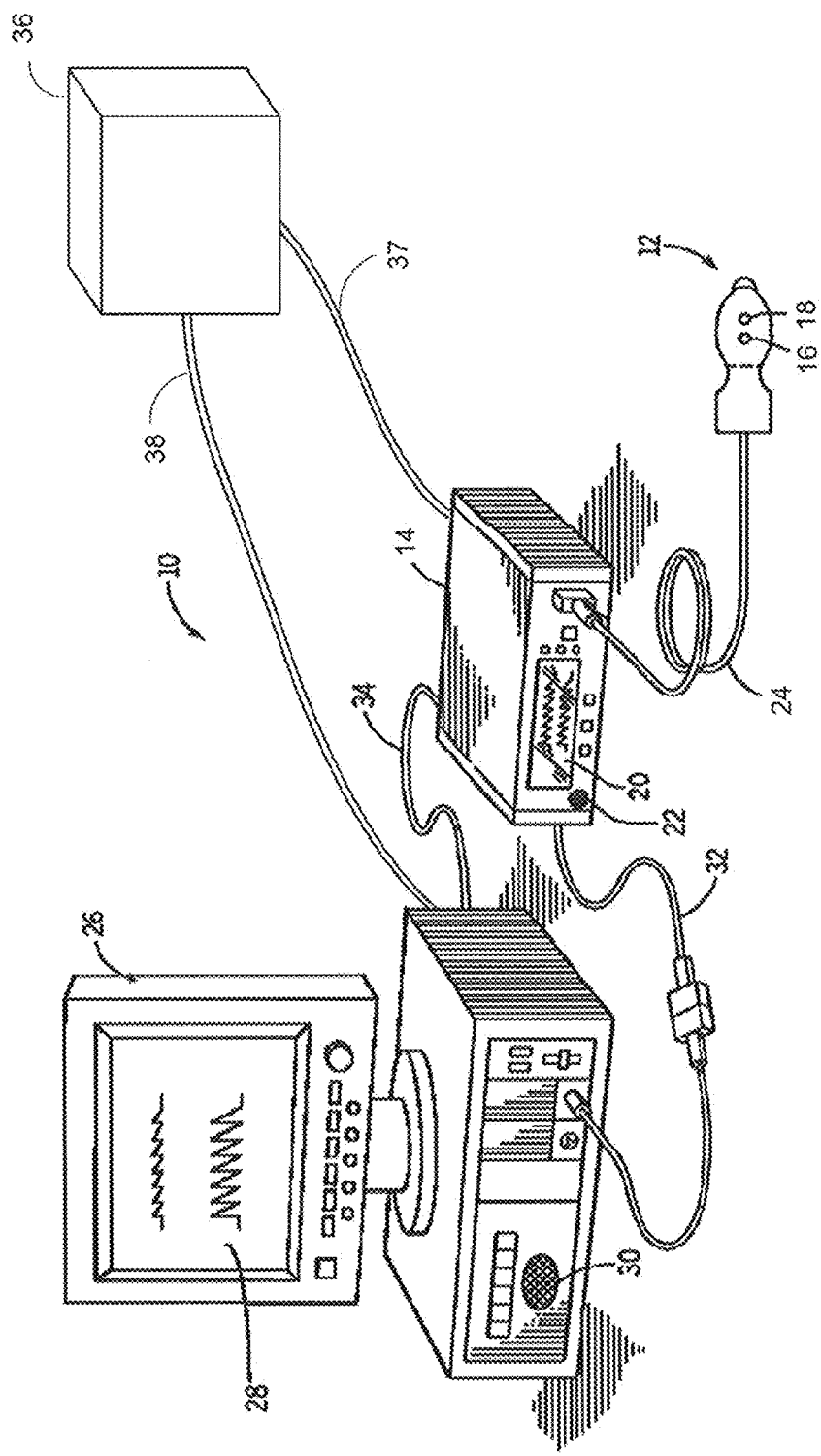
FIG. 1 shows an illustrative pulse oximetry system in accordance with an embodiment.

Medical imaging is a technique used to create images of the human body or parts thereof for the purpose of scientific study or to diagnose or examine disease. Medical imaging scans may be performed by a variety of medical imaging devices and techniques to produce these images. For example, computed tomography (CT) (also known as computed axial tomography (CAT)) is a medical imaging method employing tomography, or the imaging by sections or by sectioning. CT uses digital geometry processing to generate a three-dimensional image of the inside of an object from a large series of two-dimensional X-ray images taken around a single axis of rotation. CT produces a volume of data which may be manipulated, through a process known as "windowing," in order to demonstrate various bodily structures based on their ability to block the X-ray beam. The images may be generated in the axial or transverse plane, orthogonal to the long axis of the body. The image data may also be reformatted in various planes or even as volumetric (three-dimensional) representations of structures.

Another example of an imaging technique is positron emission tomography (PET), a nuclear medicine imaging technique which produces a three-dimensional image or picture of functional processes in the body. The system detects pairs of gamma rays emitted indirectly by a tracer, a positron-emitting radionuclide, which is introduced into the body on a biologically active molecule. Images of tracer concentration in three-dimensional space within the body are then reconstructed by computer analysis. This reconstruction may be accomplished with the aid of a CT X-ray scan performed on the patient during the same session.

Magnetic resonance imaging (MRI) is another medical imaging technique, most commonly used in radiology to visualize the internal structure and function of the body. MRI provides greater contrast between the different soft tissues of the body than CT does, making it especially useful in neurological (brain), musculoskeletal, cardiovascular, and oncological imaging. Unlike CT, it uses no ionizing radiation, but uses a powerful magnetic field to align the nuclear magnetization of atoms in the body, most commonly hydrogen. Radio frequency fields are used to systematically alter the alignment of this magnetization, causing the nuclei to produce a rotating magnetic field detectable by the scanner. This signal can be manipulated by additional magnetic fields to build up enough information to construct an image of the body.

It will be understood that the present disclosure is applicable to any suitable imaging device, and the above techniques are described merely for illustrative purposes. The present disclosure has wide applicability to other imaging techniques including, but not limited to other medical imaging techniques (e.g., electron microscopy, fluoroscopy, projectional radiography, photoacoustic imaging, infrared imaging thermography, orthopantomography, ultrasonography, or any other suitable medical imaging technique), non-destructive materials testing techniques, any other suitable imaging technique, and any combination thereof.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda,t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{\frac{dI}{dt}}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R) - I(t_1,\lambda_R)}{I(t_1,\lambda_R)}}{\frac{I(t_2,\lambda_{IR}) - I(t_1,\lambda_{IR})}{I(t_1,\lambda_{IR})}} \quad (7)$$

$$= \frac{[I(t_2,\lambda_R) - I(t_1,\lambda_R)]I(t_1,\lambda_{IR})}{[I(t_2,\lambda_{IR}) - I(t_1,\lambda_{IR})]I(t_1,\lambda_R)}$$

$$= R$$

which defines a cluster of points whose slope of y versus x will give R where $$x(t) = [I(t_2,\lambda_{IR}) - I(t_1,\lambda_{IR})]I(t_1,\lambda_R)$$

$$y(t) = [I(t_2,\lambda_R) - I(t_1,\lambda_R)]I(t_1,\lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at one or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

In the illustrated embodiment, pulse oximetry system 10 may also include imaging device 36, which generates imaging data of the patient. Imaging device 36 may be a computed tomography (CT) device, positron emission tomography (PET) device, magnetic resonance imaging (MRI) device, any suitable imaging device, or any combination thereof that generates imaging data.

Imaging device 36 may be communicatively coupled to pulse oximetry monitor 14 via a cable 37 that is coupled to a digital communications port or may communicate wirelessly (not shown). Alternatively or in addition, imaging device 36 may be communicatively coupled to multi-parameter patient monitor 26 via a cable 38 that is coupled to a digital communications port or may communicate wirelessly (not shown).

Figure 2:
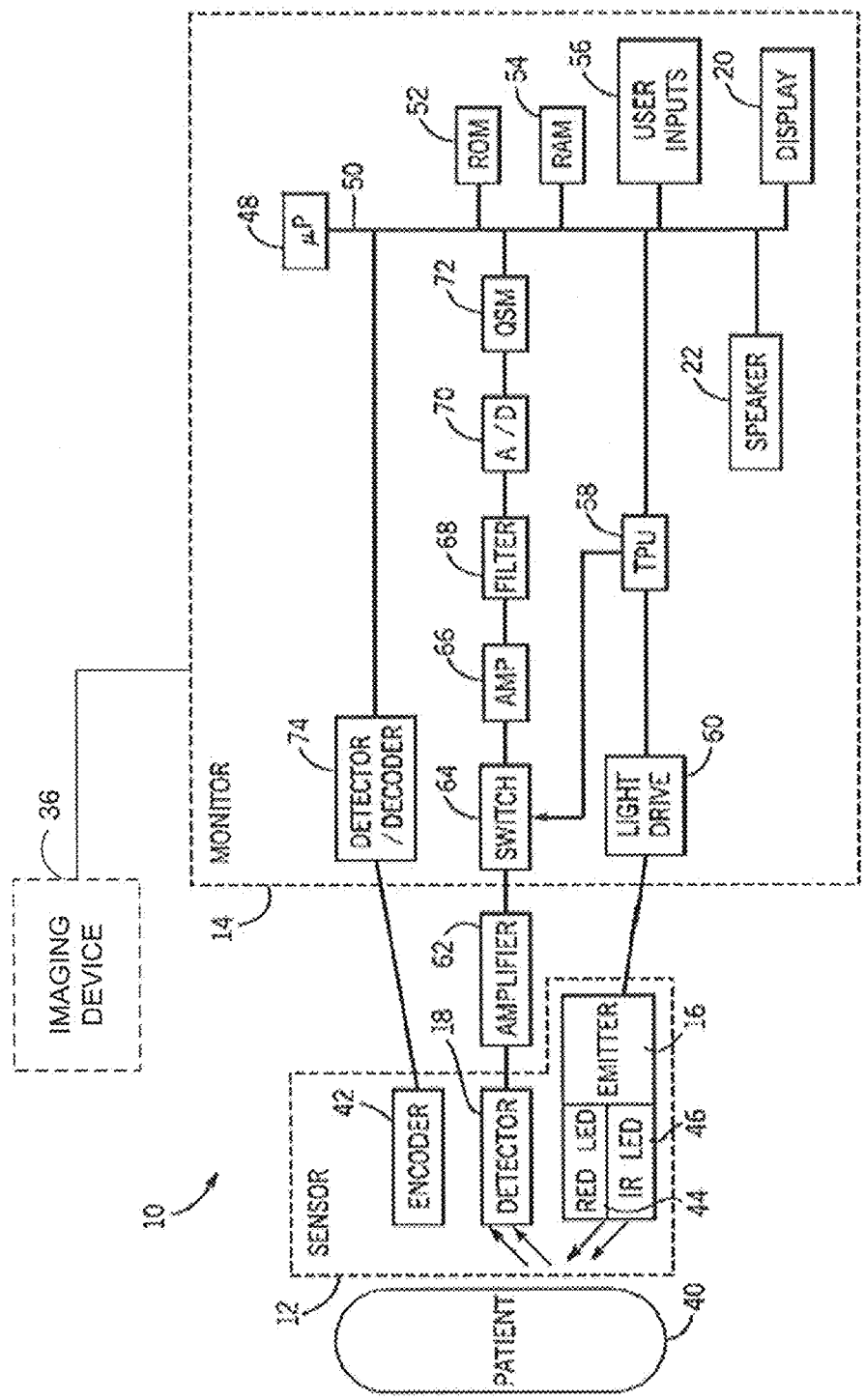
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelength of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

In an embodiment, imaging device 36 may be communicatively coupled to monitor 14. Microprocessor 48 may determine the patient's physiological process information, such as where the patient is in the respiratory and/or cardiac cycle, and display imaging data produced by imaging device 36 on display 20.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a,b) = \frac{1}{\sqrt{a}} \int_{-\infty}^{+\infty} x(t)\psi^*\left(\frac{t-b}{a}\right)dt \quad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \quad (10)$$

where '||' is the modulus operator. The scalogram may be resealed for useful purposes. One common resealing is defined as $$S_R(a,b) = \frac{|T(a,b)|^2}{a} \quad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of resealing including, but not limited to, the original unsealed wavelet representation, linear resealing, any power of the modulus of the wavelet transform, or any other suitable resealing. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t)=\pi^{-1/4}(e^{i2\pi f_0 t}-e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
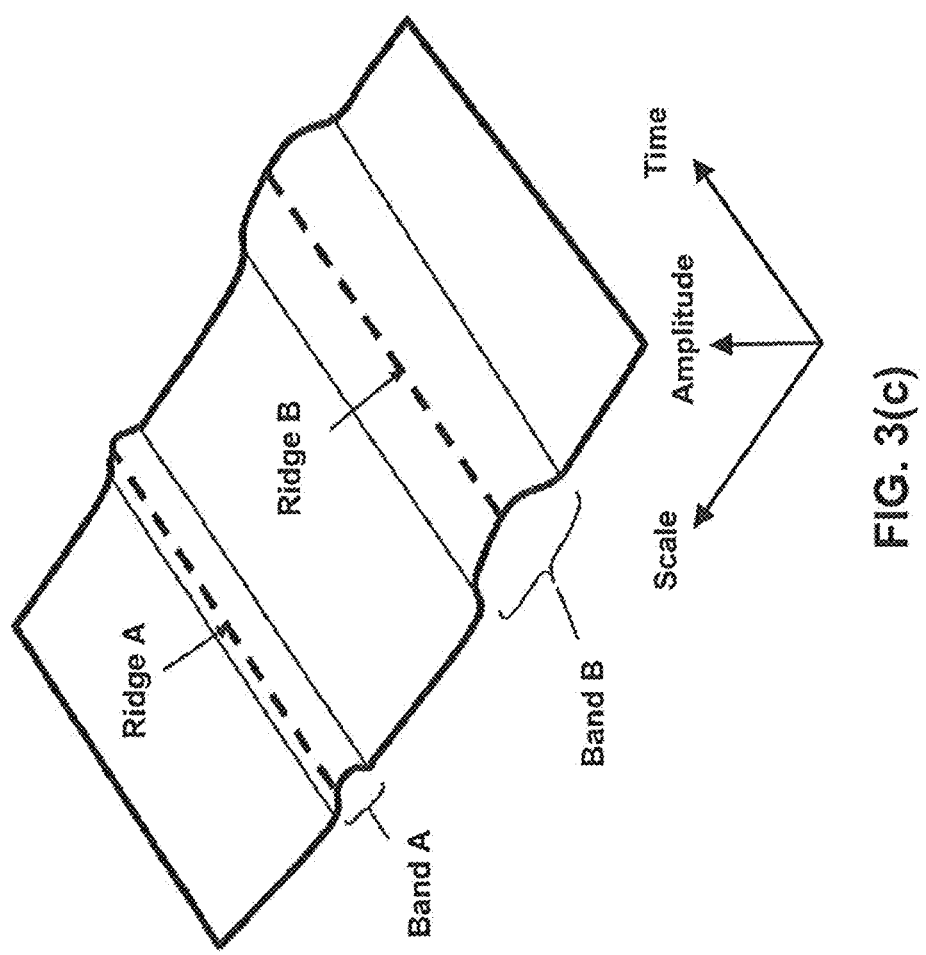
FIG. 3(c) shows an illustrative scalogram derived from a signal containing two pertinent components in accordance with an embodiment.
Figure 3D:
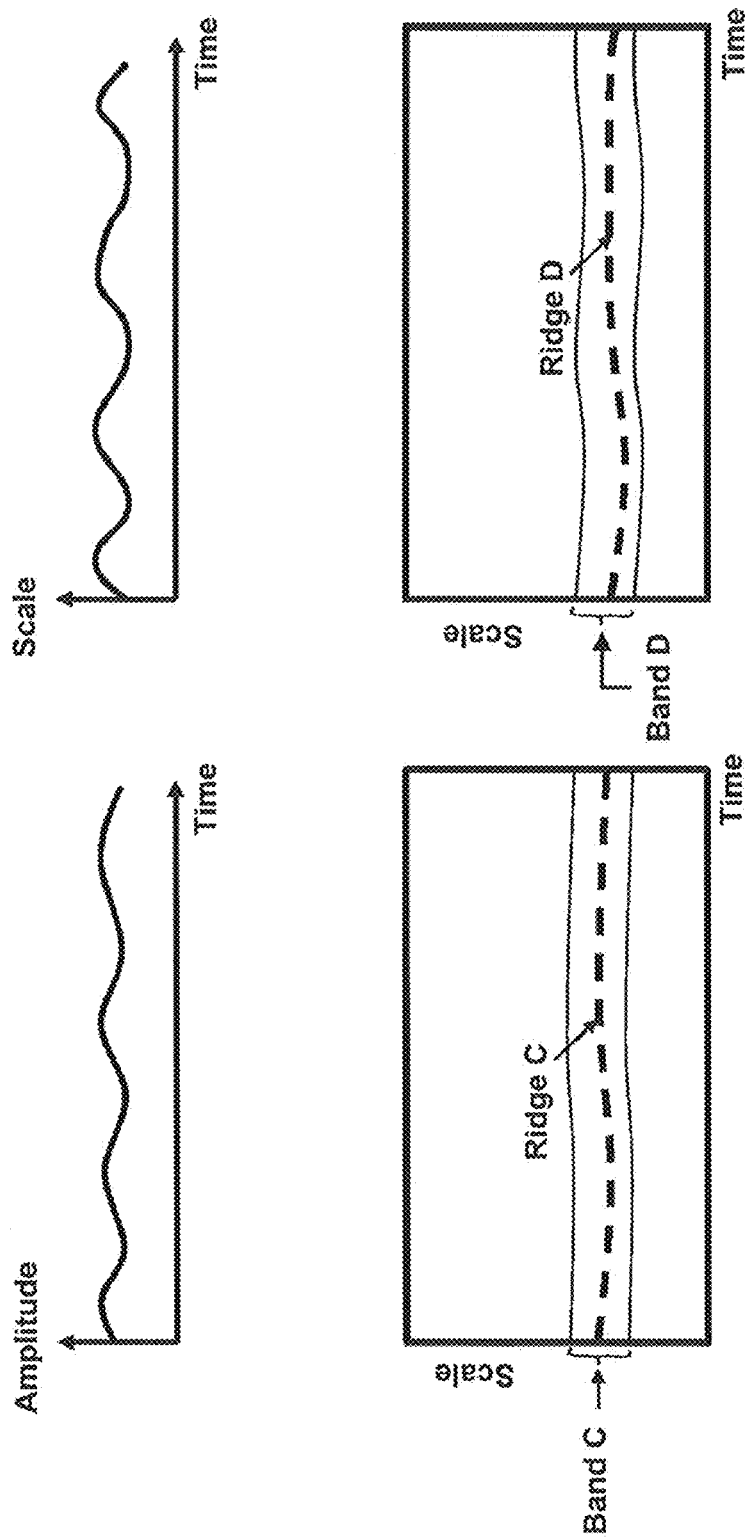
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as $$x(t) = \frac{1}{C_g} \int_{-\infty}^{\infty} \int_0^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
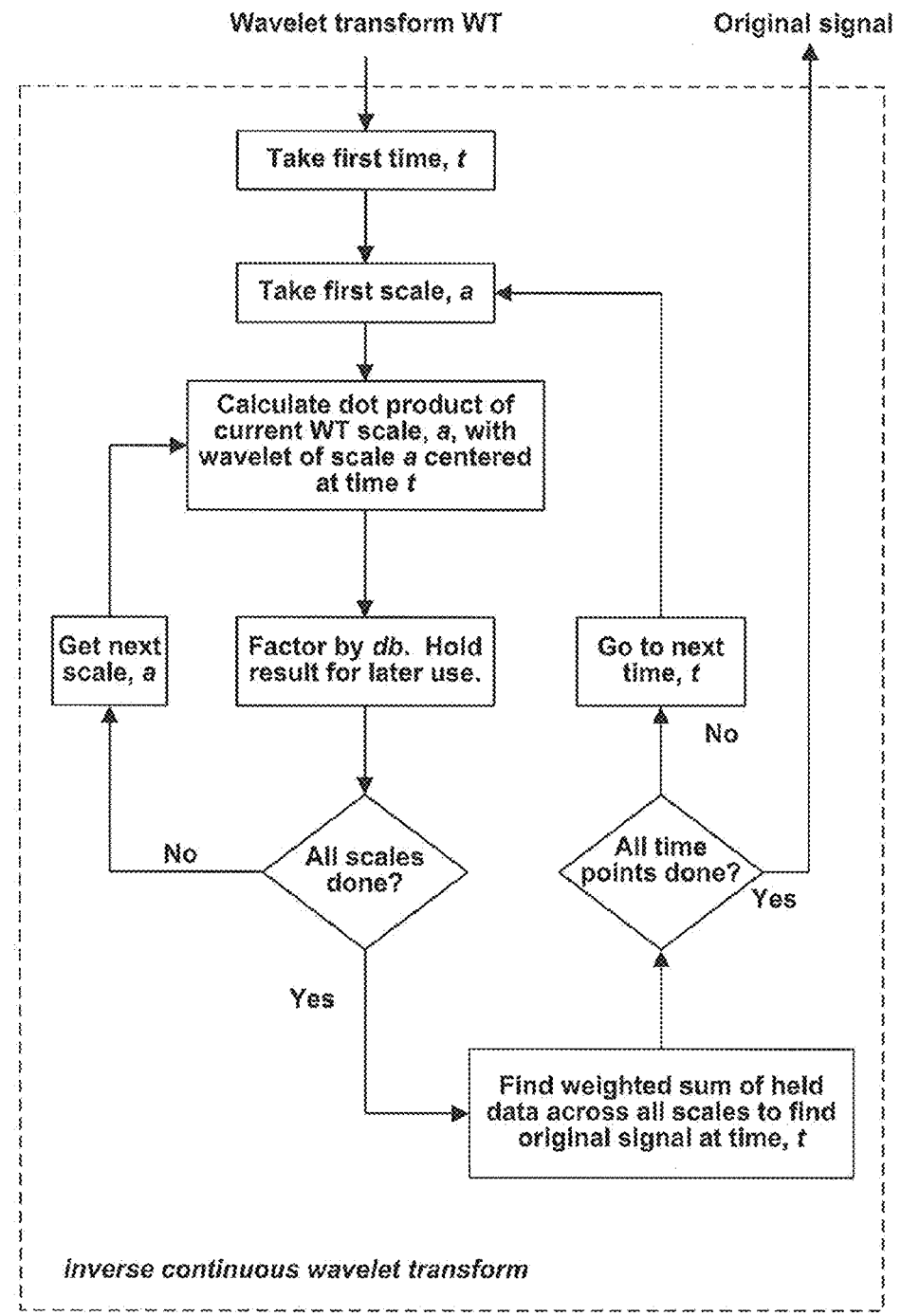
FIGS. 3(e) and 3(f) are flow charts of illustrative steps involved in performing an inverse continuous wavelet transform in accordance with an embodiment.
Figure 3F:
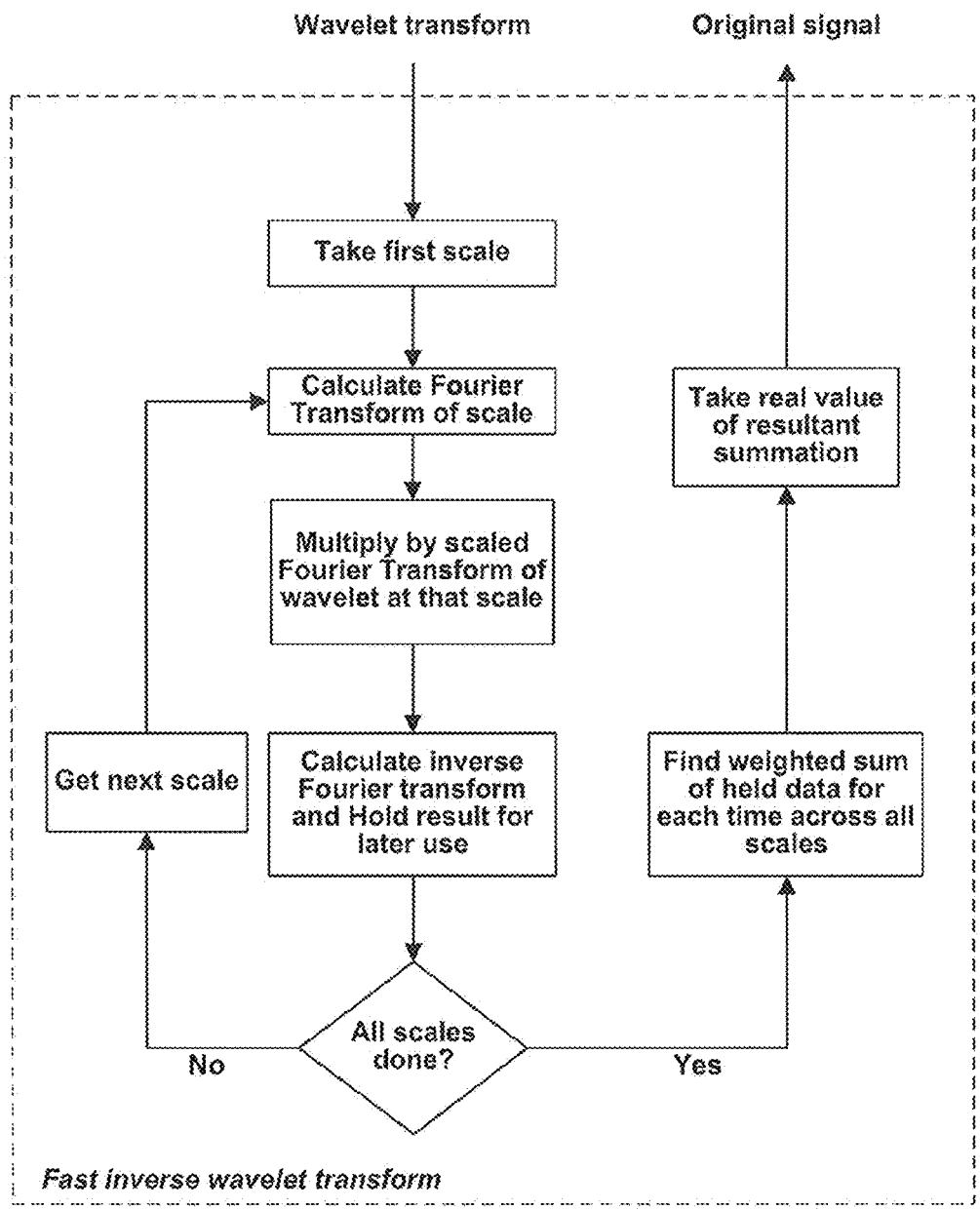

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
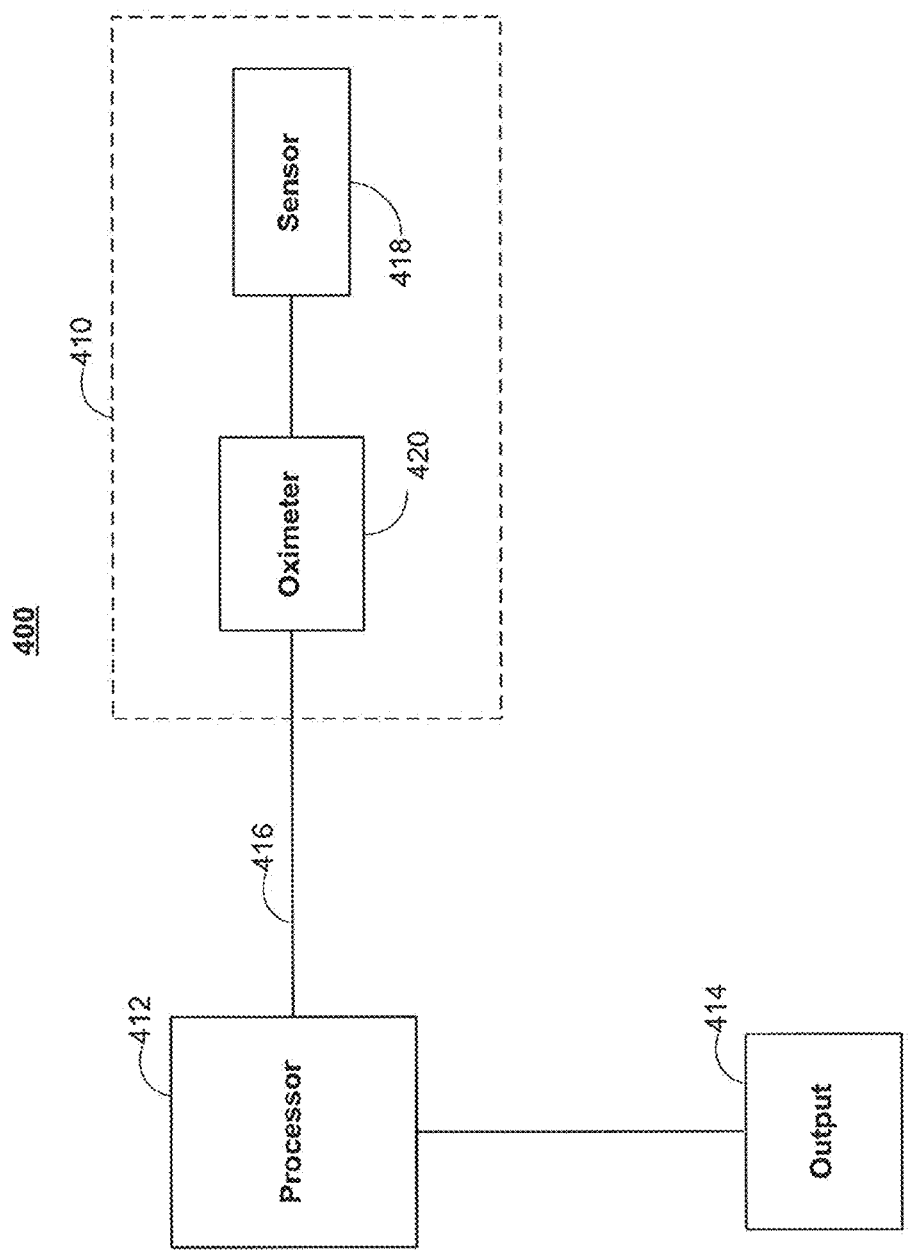
FIG. 4 is a block diagram of an illustrative continuous wavelet processing system in accordance with an embodiment.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

In an embodiment, the present disclosure may be used to automatically gate an imaging device. By analyzing plethysmographic waveform data, a signal may be derived that describes where the patient is in the respiratory and/or cardiac cycle. This derived signal may be used to gate the imaging data acquired during an imaging scan, such as a CT scan, a PET scan, or an MRI scan.

Figure 5:
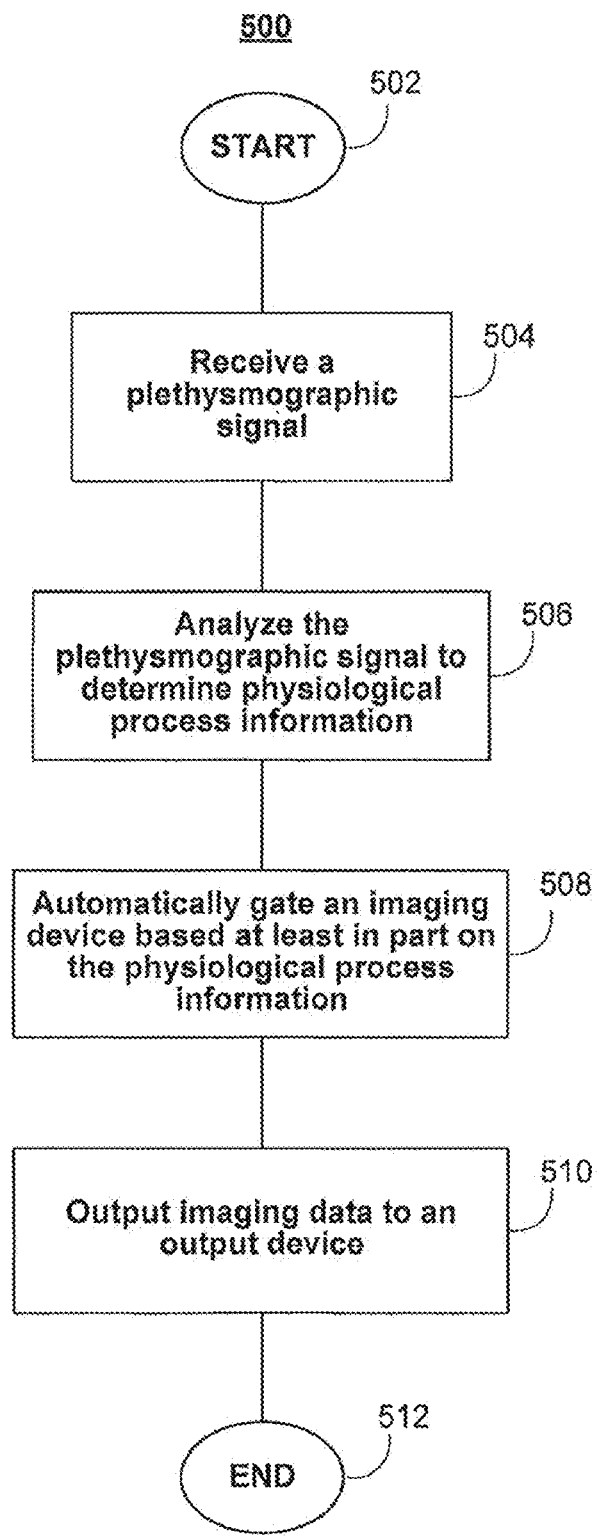
FIG. 5 is a flow chart of illustrative steps involved in automatically gating an imaging device in accordance with an embodiment.

FIG. 5 is a flow chart of illustrative steps involved in automatically gating an imaging device in accordance with some embodiments. Process 500 may begin at step 502. At step 504, a plethysmographic signal (e.g., a PPG signal) may be obtained from sensor 12 that may be coupled to patient 40 (FIG. 2). Alternatively, the PPG signal may be obtained from input signal generator 410, which may include oximeter 420 coupled to sensor 418, which may provide as input signal 416 (FIG. 4) a PPG signal. In an embodiment, the PPG signal may be obtained from patient 40 using sensor 12 or input signal generator 410 in real time. In an embodiment, the PPG signal may have been stored in ROM 52, RAM 54, and/or QSM 72 (FIG. 2) in the past and may be accessed by microprocessor 48 within monitor 14 to be processed. Although the present disclosure is provided in the context a pulse oximetry system that relies on two or more wavelength of radiation, it will be understood that the gating features described herein may be based on a system that uses a single wavelength of radiation.

Figure 6:
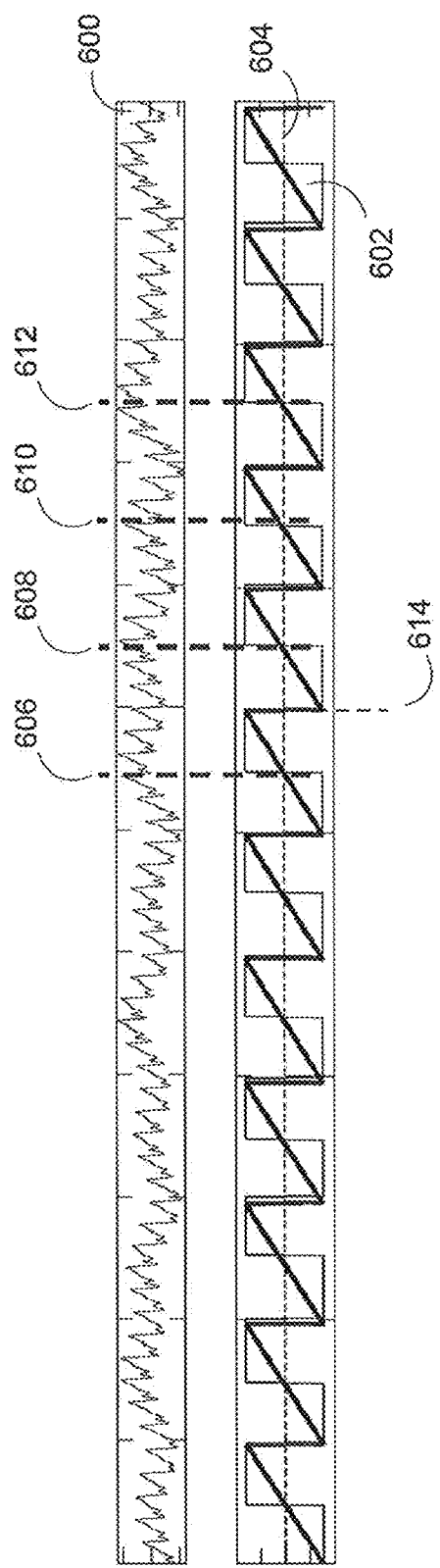
FIG. 6 shows an illustrative PPG signal and a corresponding phase plot in accordance with an embodiment.

In an embodiment, at step 506, the received signal may be analyzed to determine physiological process information. For example, a PPG signal may be transformed using a continuous wavelet transform as described above with respect to, for example, FIG. 3(a)-(d). Processor 412 or microprocessor 48 may perform the calculations associated with the continuous wavelet transform of the PPG signal. FIG. 6 shows an illustrative PPG signal collected from a patient and a corresponding phase plot in accordance with an embodiment. A plethysmographic signal, such as PPG signal 600, may be received in step 504 and analyzed in step 506 to determine physiological process information by, for example, analyzing baseline modulation. The PPG signal baseline of PPG signal 600 may exhibit undulations due to respiration. PPG signal 600 may be transformed using a continuous wavelet transform to generate the phase of the respiration band in wavelet space, such as phase plot 602. Zero phase 604 aligns with the peak of the undulations in PPG signal 600. Zero phase 604 may intersect with phase plot 602 at, for example, points 606, 608, 610, and 612, indicating the beginning of a respiration cycle of a patient (i.e., the maximum point of exhalation and the beginning of inspiration). Additionally, the maximum point of inspiration and the beginning of exhalation in the respiration cycle may be calculated, such as at point 614 in the respiration cycle between points 606 and 608. Therefore, PPG signal 600 and corresponding phase plot 602 may be used to determine at what point the patient is in the respiratory cycle. In this way, the instantaneous phase of the respiratory cycle features may be tracked in time, allowing the phase of the respiratory cycle features to be decoupled from the other features in the signal at other scales. Thus, an accurate measure of the instantaneous phase of the respiratory cycle may be made. For example, the imaging device my be focused on a 5 mm tumor which moves 10 mm during the respiration cycle, a gated image synchronized on the dwell or stationary period of the respiratory cycle may present a true image of a 5 mm tumor while an ungated device may provide a blurred image of a low activity tumor with extent over 15 mm. In a further example, breaths identified as being atypical, for example a deep inhalation, may be rejected from the imaging process entirely.

Figure 7:
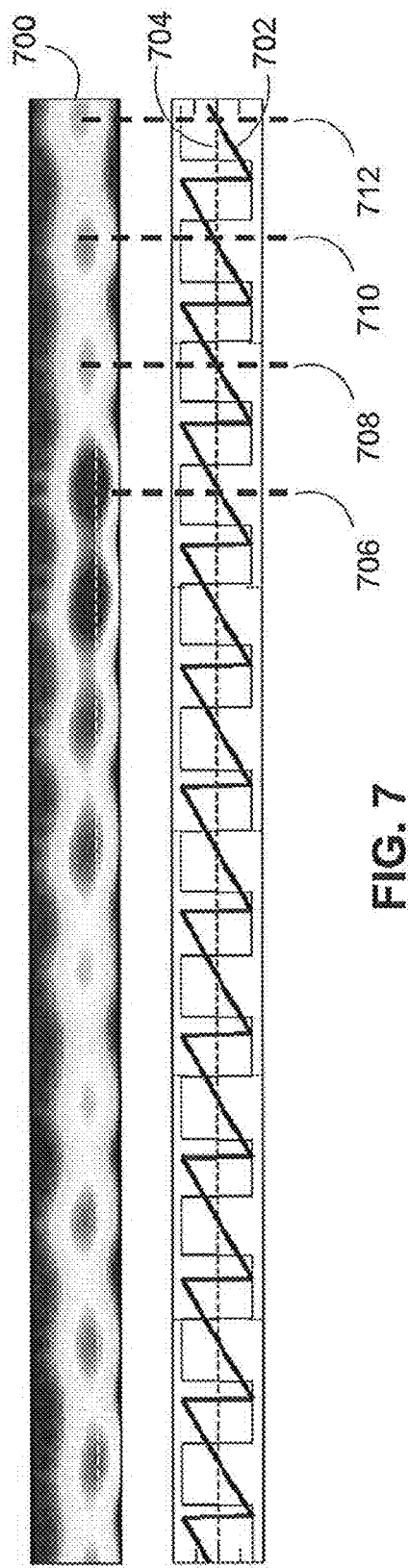
FIG. 7 shows an illustrative view of a scalogram and corresponding phase signal in accordance with an embodiment.

In an embodiment, at step 506, a scalogram may be generated based at least in part on the wavelet-transformed signal. For example, processor 412 or microprocessor 48 may perform the calculations associated with the derivation of the scalogram. FIG. 7 shows an illustrative view of a scalogram and corresponding phase signal in accordance with an embodiment. A PPG signal may be transformed using a continuous wavelet transform and a scalogram that exhibits a distinct pulse band, such as scalogram 700, may be generated. Further, the phase of the pulse band modulations, such as phase plot 702, may be generated by performing a secondary wavelet transform on the pulse band ridge points. Zero phase 704 may intersect with phase plot 702 at, for example, points 706, 708, 710, and 712, indicating the beginning of a cardiac cycle of a patient. Therefore, scalogram 700 and corresponding phase plot 702 may be used to determine at what point the patient is in the cardiac cycle. In this way, the instantaneous phase of the cardiac cycle features may be tracked in time, allowing the phase of the cardiac cycle features to be decoupled from the other features in the signal at other scales. Thus, an accurate measure of the instantaneous phase of the cardiac cycle may be made.

Figure 8:
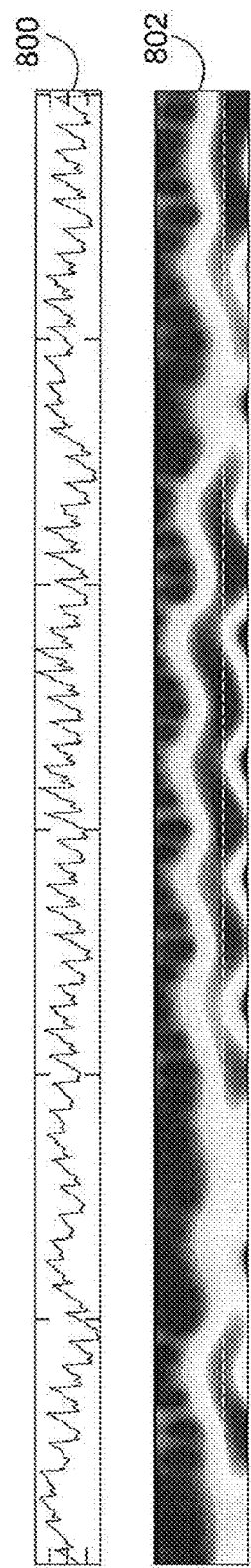
FIG. 8 an illustrative PPG signal and corresponding scalogram exhibiting respiratory sinus arrhythmia in accordance with an embodiment.

Other features of the wavelet transform or the scalogram may be used to calculate physiological process information. For example, the breathing brand of the scalogram, such as breathing band 304 in FIG. 3(b) may be used to derive a phase plot and calculate the instantaneous phase of the respiratory cycle. Because of the time-scale nature of the transform phase, instantaneous phase values corresponding to the breathing band or the pulse band may be tracked as the respiration rate or pulse rate varies. Any other suitable techniques to track sudden changes in respiration rate or pulse rate may be used, including, for example, the use of average values of phase across time and/or frequency. Other features in the wavelet transformed signal may also be used to track respiratory or cardiac cycle information including the real and/or imaginary parts of the transform at the scales of interest. FIG. 8 shows an illustrative view of a scalogram exhibiting respiratory sinus arrhythmia (RSA) in accordance with an embodiment. A plethysmographic signal, such as PPG signal 800, may be received in step 504 and analyzed in step 506 to determine physiological process information by analyzing RSA information. Scalogram 802 may be generated from PPG signal 800 and inspected for its phase relationship to respiration. The RSA phase may also be mapped via a functional relationship of the patient's actual respiration phase, e.g., each point in the phase of the respiratory sinus arrhythmia modulation may be mapped to the corresponding phase of the patient's actual respiration cycle. In this way the RSA component may be used to determine respiratory phase for use in gating.

It will be understood that any combination of one or more of the baseline modulation, the respiratory band information, the pulse band information, and/or the RSA information may be used to determine physiological process information in a patient. In an embodiment, the physiological process information may be stored in ROM 52, RAM 54, QSM 72, and/or microprocessor 48 within monitor 14 (FIG. 2) and may be accessed by microprocessor 48 to be processed.

In an embodiment, in step 508, the physiological process information generated in step 506 may be used to gate an imaging device. The imaging device, such as imaging device 36 in FIG. 2, may be a computed tomography (CT) device, a positron emission tomography (PET) device, a magnetic resonance imaging (MRI) device, any suitable imaging device, or any combination thereof. In an embodiment, the imaging device may produce imaging data that may be synchronized in real-time with the respiratory and/or cardiac cycle information derived in step 506 in order to "freeze" the motion of internal organs during the scan. In an embodiment, the scanner may be synchronized with the gating device in order to minimize a radiation dose to the patient. For example, in a gated CT image, the CT radiation source may be switched on only when the patient is in the desired phase of the respiratory and/or cardiac cycle. Further, the CT source may be switched off when patient motion is detected. In an embodiment, the imaging data may be stored with a time marker in a datafile in imaging device 36, or in ROM 52, RAM 54, QSM 72, and/or microprocessor 48 within monitor 14 (FIG. 2). The imaging data and physiological process information may be accessed by microprocessor 48 to be processed, and using the time marker information, the imaging data may be synchronized with the respiratory and/or cardiac cycle information derived and stored in step 506 in order to "freeze" the motion of internal organs during the scan. In an embodiment, the imaging data may be taken at the same time in the respiratory and/or cardiac cycle. For example, the imaging data may be taken at the beginning of inspiration, the beginning of expiration, any other suitable point in the respiratory and/or cardiac cycle, or any combination thereof. Further, it may be desirable to identify the longest periods of "dwell time" in which internal organs are relatively stationary. Picking the longest periods of dwell time may allow the total scan time to be minimized while collecting sufficient image data with organs "frozen." For example, these periods may be from about 90% of maximum exhalation until the start of the next inhalation (respiratory), and approximately the last 50% of the cardiac cycle before the next beat starts.

In an embodiment, the imaging data may include supplemental data such as information about where in the respiratory and/or cardiac cycle the image was taken. The supplemental data may include physiological parameters at the time the image was taken, oxygen saturation information at the time the image was taken, any other suitable information, or any combination thereof.

Figure 9:
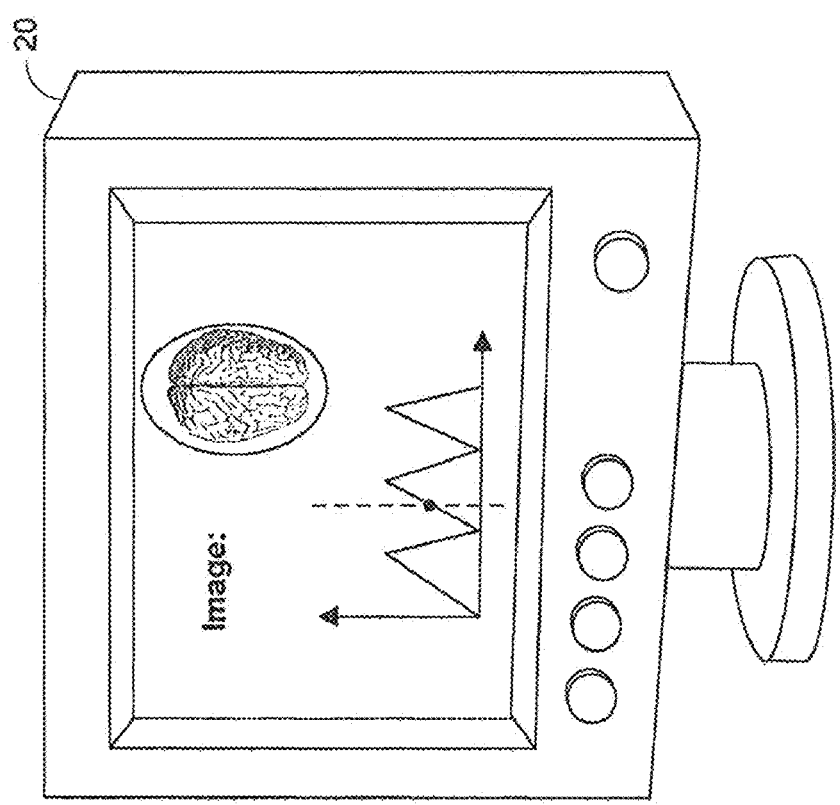
FIG. 9 shows an illustrative output device displaying imaging data in accordance with an embodiment.

In an embodiment, in step 510, the gated imaging data produced in step 508 may be outputted to display 20 (FIG. 2), multi-parameter patient monitor 26 (FIG. 1), any other display device communicatively coupled to system 10, or any combination thereof. For example, the imaging data may be displayed on a display such as display 20, as illustrated by FIG. 9. In an embodiment, a sequence of gated imaging data taken at the same point in the respiratory and/or cardiac cycle may be generated and displayed on a display such as display 20.

In an embodiment, the physiological process information from step 506 may also be displayed on an output device. Instead of or in addition to the above, supplemental information such as information about where in the respiratory and/or cardiac cycle the image was taken may be displayed on an output device. The gated imaging data, the physiological process information, and/or the supplemental information may also be outputted to any other suitable output device, such as a computer, a computer-readable medium, a printer, any other suitable output device, or any combination thereof. Following the output of the imaging data in step 510, process 500 may advance to step 512 and end.

The foregoing is merely illustrative of the principles of this disclosure and various modifications may be made by those skilled in the art without departing from the scope and spirit of the disclosure.

What is claimed is:

1. A method of obtaining imaging data from a patient, the method comprising:
   receiving from a sensor that comprises at least one light emitter and a detector a plethysmographic signal that represents light that has been at least partially absorbed by tissue of the patient;
   analyzing with a processor the plethysmographic signal to determine physiological process information; and
   automatically gating an imaging device based at least in part on the physiological process information.

2. The method of claim 1, wherein the imaging device comprises a computed tomography device, a positron emission tomography device, and/or a magnetic resonance imaging device, and/or combinations thereof.

3. The method of claim 1, wherein the analyzing comprises determining physiological process information based at least in part on the plethysmographic signal.

4. The method of claim 1, wherein the analyzing comprises determining cardiac cycle information based at least in part on the plethysmographic signal.

5. The method of claim 1, wherein the analyzing comprises transforming the plethysmographic signal based at least in part on a continuous wavelet transform.

6. The method of claim 1, wherein the analyzing comprises identifying periods of voluntary or involuntary patient movement.

7. The method of claim 1, further comprising outputting the imaging data to an output device.

8. A system for gating imaging data of a patient, the system comprising:
   a sensor attached to the patient capable of generating a plethysmographic signal that represents light that has been at least partially absorbed by tissue of the patient, wherein the sensor comprises at least one light emitter and a detector;
   an imaging device capable of generating an imaging signal; and
   a processor coupled to the sensor and to the imaging device capable of analyzing the plethysmographic signal to determine physiological process information, wherein the imaging device is automatically gated based at least in part on the physiological process information.

9. The system of claim 8, wherein the imaging device comprises a computed tomography device, a positron emission tomography device, and/or a magnetic resonance imaging device, and/or combinations thereof.

10. The system of claim 8, wherein the analyzing comprises determining physiological process information based at least in part on the plethysmographic signal.

11. The system of claim 8, wherein the analyzing comprises determining cardiac cycle information based at least in part on the plethysmographic signal.

12. The system of claim 8, wherein the analyzing comprises transforming the plethysmographic signal based at least in part on a continuous wavelet transform.

13. The system of claim 8, wherein the analyzing comprises identifying periods of voluntary or involuntary patient movement.

14. The system of claim 8, further comprising outputting the imaging data to an output device.

15. A non-transitory computer-readable medium for gating imaging data, the non-transitory computer-readable medium having computer program instructions recorded thereon for:
receiving from a sensor that comprises at least one light emitter and a detector a plethysmographic signal that represents light that has been at least partially absorbed by tissue of the patient;
analyzing a plethysmographic signal to determine physiological process information; and
automatically gating an imaging device based at least in part on the physiological process information.

16. The non-transitory computer-readable medium of claim 15, wherein the imaging device comprises a computed tomography device, a positron emission tomography device; and/or a magnetic resonance imaging device, and/or combinations thereof.

17. The non-transitory computer-readable medium of claim 15, wherein the analyzing comprises determining physiological process information based at least in part on the plethysmographic signal.

18. The non-transitory computer-readable medium of claim 15, wherein the analyzing comprises determining cardiac cycle information based at least in part on the plethysmographic signal.

19. The non-transitory computer-readable medium of claim 15, wherein the analyzing comprises transforming the plethysmographic signal based at least in part on a continuous wavelet transform.

20. The non-transitory computer-readable medium of claim 15; further comprising outputting the imaging data to an output device.

* * * * *